(12) United States Patent
Peters et al.

(10) Patent No.: US 7,800,378 B2
(45) Date of Patent: Sep. 21, 2010

(54) MICROWAVE RESONATOR FOR OR ON A TEXTILE MACHINE, ESPECIALLY A CARD, DRAW FRAME, COMBING MACHINE OR THE LIKE

(75) Inventors: Steffen Peters, Linnich-Rurdorf (DE); Frank Sundermeier, Bad Oeynhausen (DE)

(73) Assignee: Fa. Trützschler GmbH & Co.Kg, Mönchengladbach (DE)

( * ) Notice: Subject to any disclaimer, the term of this patent is extended or adjusted under 35 U.S.C. 154(b) by 344 days.

(21) Appl. No.: 12/000,166

(22) Filed: Dec. 10, 2007

(65) Prior Publication Data
US 2008/0148823 A1 Jun. 26, 2008

(30) Foreign Application Priority Data
Dec. 22, 2006 (DE) .................. 10 2006 062 339

(51) Int. Cl.
*G01R 27/04* (2006.01)
(52) U.S. Cl. .................. 324/636; 324/640; 324/634
(58) Field of Classification Search ............. 324/636, 324/640, 643, 634
See application file for complete search history.

(56) References Cited

U.S. PATENT DOCUMENTS

| | | | |
|---|---|---|---|
| 3,137,828 A | 6/1964 | Gerig et al. | |
| 4,885,527 A | 12/1989 | Lacombe et al. | |
| 5,103,180 A | 4/1992 | Lahitte et al. | |
| 6,204,603 B1 * | 3/2001 | Spitzl et al. ............ | 315/111.21 |
| 2001/0000946 A1 * | 5/2001 | Moeller et al. ............. | 324/640 |
| 2006/0071670 A1 | 4/2006 | Gohler et al. | |

FOREIGN PATENT DOCUMENTS

| | | |
|---|---|---|
| DE | 2321770 A1 | 3/1975 |
| DE | 10313964 A1 | 10/2004 |
| DE | 10334144 A1 | 1/2005 |
| DE | 10 2005 009 159 | 8/2006 |
| EP | 1114299 | 3/2000 |
| EP | 1454133 | 6/2003 |
| GB | 2 400 443 A | 10/2004 |
| GB | 2 411 240 A | 8/2005 |
| WO | WO 2005/003747 A | 1/2005 |

OTHER PUBLICATIONS

German Search Report dated Jun. 26, 2007, issued in DE 10 2006 062 339.8.
UK Search Report, dated Mar. 7, 2008, issued on British Application No. GB0724882.6.

* cited by examiner

*Primary Examiner*—Vincent Q Nguyen
(74) *Attorney, Agent, or Firm*—Venable LLP; Robert Kinberg; Steven J. Schwarz

(57) ABSTRACT

A microwave resonator for or on a textile machine, especially a card, draw frame, combing machine or the like, for attachment to a measuring device for measuring the mass and/or moisture content of textile fiber material conveyable continuously through a resonator chamber, has a housing with wall elements, wherein through-openings in spaced wall elements lying opposite one another are coaxially connected by a tubular element and the interior space of the housing is hollow. In order substantially to simplify manufacture and permit an uninterrupted resonance field, the housing comprises a hollow profile with profile walls in which at least one tubular element connects through-openings in opposite profile walls with each other.

26 Claims, 9 Drawing Sheets

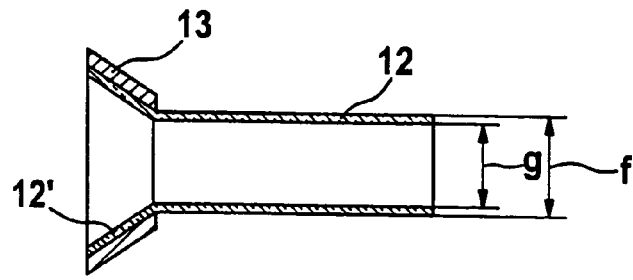
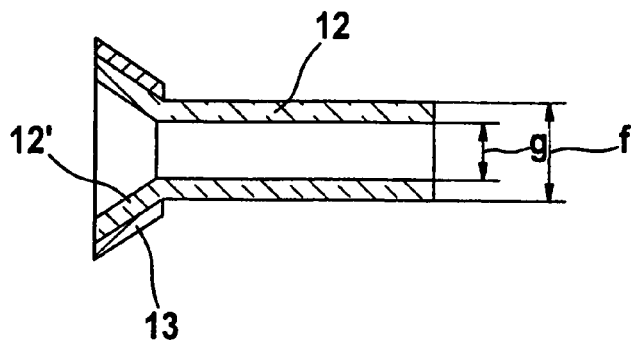
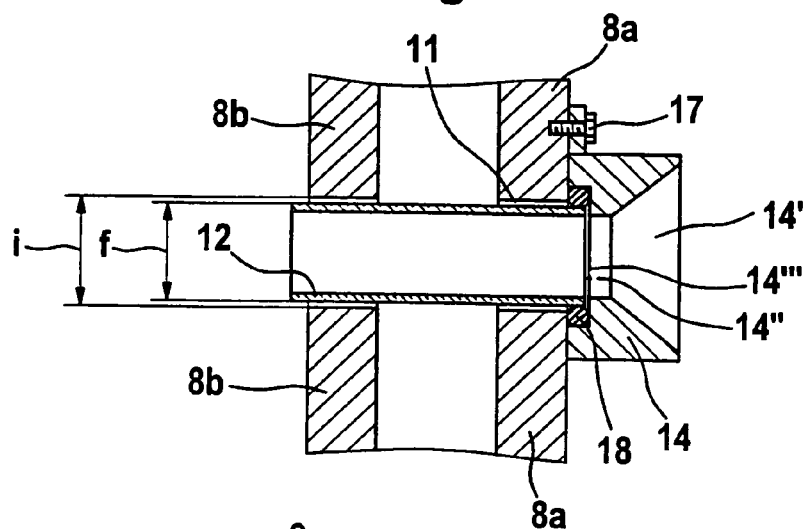
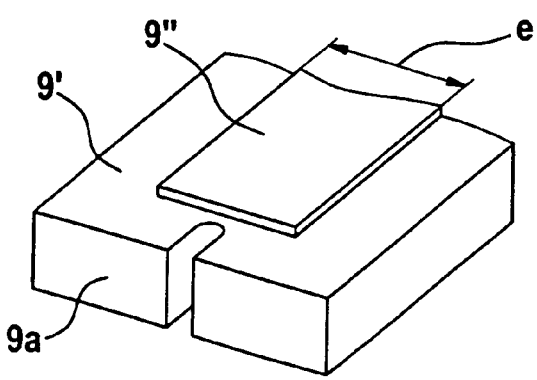

MICROWAVE RESONATOR FOR OR ON A TEXTILE MACHINE, ESPECIALLY A CARD, DRAW FRAME, COMBING MACHINE OR THE LIKE

CROSS REFERENCE TO RELATED APPLICATION

This application claims priority from German Patent Application No. 10 2006 062 339.8 dated Dec. 22, 2006, the entire disclosure of which is incorporated herein by reference.

BACKGROUND OF THE INVENTION

The invention relates to a microwave resonator for or on a textile machine, especially a card, draw frame, combing machine or the like, for attachment to a measuring device for measuring the mass and/or moisture content of textile fibre material conveyable continuously through a resonator chamber.

In practice, methods and apparatuses are used to detect at least one property of a material by evaluating the detuning of a microwave-fed HF resonator caused by the presence of the material; a high-frequency signal influenced by the material is tapped off the resonator, and the resonant frequency shift and attenuation of the signal compared with a signal unaffected by the material is determined. The purpose of determining the properties is in particular to obtain signals from materials such as textile fibre material, for example, cotton and/or synthetic fibres, these signals being subject to further processing to give signals corresponding to the mass and/or moisture content of the textile fibre material, which can be used for a control and/or regulation of a textile machine.

In a known microwave resonator chamber used in the monitoring of textile fibre material, a housing with wall elements is present, wherein-through-openings in spaced wall elements lying opposite each other are coaxially connected by a tubular element and the interior space of the housing is hollow. In the case of one known microwave resonator (WO 2005/003747 A), the resonator is arranged in a platform-like supporting construction. The supporting construction comprises for that purpose a cylindrical central recess. A wall element in the form of a flat cylindrical disc with screw seats at its edge that align with complementary blind bores in the supporting construction is positioned on the recess. Hexagon screws are screwed into these bores, which each have an internal thread, in order to screw the wall element to the supporting construction. The wall element positioned on the recess creates a resonator chamber of the microwave resonator into which microwaves are injected by means of an injection means and extracted by means of an output means. Both the injection and output means, which are, for example, of rod form, project from the outside into the resonator chamber through complementary bores in the wall element. A dielectric substantially in the form of a hollow-cylindrical guide tube and comprising an electrically non-conducting material is inserted in the resonator chamber. The dielectric has at each end face an external bulge, with which it lies in a through-opening of the wall element on the one hand and a through-opening in the supporting construction on the other hand. A fibre sliver is guided linearly through the resonator chamber and subsequently through a sliver funnel. The sliver funnel is held in an annular bead of the supporting construction and has an annular groove for that purpose. It is a considerable disadvantage that the central recess for each microwave resonator has to be shaped in the platform-like supporting construction, for example, by a machining process such as milling or the like. This is associated with a considerable amount of time and energy in production terms. Another particular disadvantage is that the wall element (flat cylindrical disc) positioned on the recess forms the closure element for the resonator chamber. The tubular element thus connects the superimposed wall element with the base wall of the supporting construction. Between the wall element and the supporting construction there is a circumferential, circular ring-shaped contact face, which has to be conductively sealed off to avoid interruption of the wall currents and hence a collapse of the microwave field. The electrical fields cause a movement of electrons, i.e. a current flow, at the surface of the inner walls of the resonator chamber. For an optimum behaviour of the microwave resonator, the surface current must flow along the shortest path and with the least possible resistance, as otherwise it builds up an electromagnetic opposing field, which attenuates the resonance field and thus leads to a lower quality of the resonator. The resonator must therefore have on its inside a surface of low peak-to-valley height (short-paths) and good conductivity. The circumferential edge of the flat cylindrical disc is a significant disruptive factor here. In addition, it is impossible to ensure a good and universally uniform contact between the flat cylindrical disc and the supporting construction, so that here too the current flow is impeded or even prevented by poor conductivity or by inadequate contact. Oxidation or contamination of the contact surface is also a possibility. If the electrical connection of individual components of the resonator is not uniform or adequate, however, an undefined behaviour of the resonator may occur under changing climatic conditions. Also, and in particular, total failure is possible, because the resonator can no longer be excited.

SUMMARY OF THE INVENTION

It is an aim of the invention to produce a microwave resonator of the kind described initially, which eliminates or mitigates the said disadvantages, which in particular allows a substantially simplified manufacture and permits an undisturbed resonance field.

The invention provides a microwave resonator for or on a textile machine for attachment to a measuring device for measuring the mass and/or moisture content of textile fibre material comprising:

a resonator chamber through which textile fibre material is conveyable continuously, having a housing with wall elements including spaced, opposed first and second wall elements;

an inlet through-opening in said first wall element and an outlet through-opening in said second wall element; and at least one tubular element coaxially connecting said inlet and outlet through-openings;

wherein the housing comprises a hollow profile with profile walls of which first and second opposite profile walls of the hollow profile form said first and second wall elements in which said connected through-openings are located.

Owing to the fact that a hollow profile having seamless profile walls is used for the housing, manufacturing expense is reduced quite considerably. Extrusion-moulded hollow profiles in particular, for example, of aluminum, render manufacture very economical. This manufacture is especially suitable for mass production. The microwave resonator is quick, simple and inexpensive to manufacture and to mount. The profile walls are of seamless construction, so that there are no interruptions on the profile walls. The inner walls in particular of hollow profiles are smooth. A further particular advantage is that the tubular element coaxially connects through-openings (inlet and outlet openings) in opposite profile walls that have no seams or the like. Because, unlike the known microwave resonator, no interruptions, edges, abutting surfaces or the like are present, an uninterrupted flow of the wall currents is ensured and hence the efficiency and the quality of the microwave resonator according to the invention is substantially improved.

Advantageously, the interior space of the housing is closable by at least one closure element (cavity resonator). The hollow profile may be produced by, for example, non-machining shaping, plastic deformation, extrusion moulding, drawing (stretch-forming), rolling or casting.

Advantageously, the hollow profile comprises a metallic material, for example, aluminum or an aluminum alloy, copper, steel or iron-nickel steel (Invar). In one preferred embodiment described below, the hollow profile is of $AlMgSiO_5$. Advantageously, a one-piece hollow profile is provided. Advantageously, a seamless hollow profile is provided. In one embodiment, however, a jointed, for example, welded, hollow profile having a subsequently machined, especially smoothed, joining seam is provided. Advantageously, the hollow profile is a profile whose cross-sectional shape encloses a closed cavity. Advantageously, the hollow profile has a closed inner wall area, which is preferably smooth.

In one embodiment, the hollow profile is a rectangular pipe (rectangular cross-section). Advantageously, the long sides of the rectangle run perpendicular to the axis of the tubular element and to the conveying direction of the textile fibre material. Advantageously, the short sides of the rectangle run parallel to the axis of the tubular element and to the conveying direction of the textile fibre material. Advantageously, the ratio of height to depth in the cavity of the resonator is about 1:6 to 10. The cavity may have a height of, for example, about 110 to 130 mm and a depth of about 12 to 18 mm.

In another embodiment, the hollow profile is a profile having a circular cross-section. In yet a further embodiment, the hollow profile is a profile having an oval, for example, elliptical, cross-section. In the case of an oval, for example, elliptical, cross-section of the cavity, the short diameter is arranged parallel and the long diameter is arranged perpendicular to the conveying direction of the textile fibre material.

Advantageously, the hollow profile is of open construction at at least one end face, preferable at both end faces. In one preferred embodiment, the hollow profile is produced by cutting to length, for example, cutting off, an extrusion-moulded semi-finished product. Advantageously, at least one end face, preferably, both end faces, of the hollow profile are closed by a closure element. Advantageously, the resonator chamber is enclosed on all sides (cavity resonator). Advantageously, the resonator chamber is enclosed by an electrically conducting layer or wall (hollow profile walls). Advantageously, the inner wall areas of the hollow profile (hollow profile walls) are provided with an electrically conducting layer. Advantageously, the inner walls (hollow profile walls) are coated for protection against oxidation. In essence, a resonator chamber closed at its end faces is advantageously provided. Advantageously, the arrangement is such that the microwave field develops in the enclosed resonator chamber. Advantageously, the abutting faces of two inner wall areas (hollow profile walls) are rounded. Advantageously, the tubular element shuts off cavity regions of the resonator. Advantageously, the tubular element is in the form of a cylinder open at both end faces. Typically, the tubular element is provided for guidance of the textile fibre material through the resonator chamber (measuring resonator). It will often be expedient to provide a reference resonator in addition to the measurement resonator. The reference resonator will in general be of the same or similar construction to the measurement resonator except that, in practice, the tubular element will be free from textile fibre material.

Advantageously, the tubular element extends substantially from the resonator inlet to the resonator outlet. Advantageously, the tubular element comprises glass or quartz glass. Advantageously, the tubular element is so fixed that it is unable to transfer any forces, especially not from the front side to the rear side of the resonator. Advantageously, a funnel-like inlet and/or outlet element (nozzle) is associated with at least one end face of the tubular element. Advantageously, the funnel-like inlet element is associated with the resonator inlet. Advantageously, the funnel-like outlet element is associated with the resonator outlet. Preferably, the funnel-like inlet and/or outlet element is arranged outside the resonator chamber.

Preferably, the funnel-like inlet and/or outlet element is arranged in the region of the outer walls of the hollow profile. Advantageously, the tubular element and the funnel-form inlet and/or outlet element comprise the same material, especially quartz or quartz glass. In some embodiments the tubular element and the funnel-like inlet element are formed in one piece. In certain embodiments, additionally or instead, the tubular element and the funnel-like inlet and/or outlet element are formed in one piece. In other embodiments, the tubular element and the funnel-like inlet and/or outlet element are formed in at least two pieces.

Advantageously, the nozzles on the inside of the through-bore have a small shoulder, which effects a secure and effectively conducting connection between the nozzles and the hollow profile. Advantageously, the closure elements for the hollow profile have a small shoulder which effects a secure and effectively conducting connection between the respective closure element and the end-face hollow profile. Advantageously, there can be used tubular elements having different diameters of the interior space thereof. There may be used inlet and/or outlet funnel elements with different diameters of the interior space thereof. Advantageously, the closure elements and the hollow profile are connected with each other. Advantageously, at least one closure element is removable and reaffixable. The closure elements may be releasably connected with each other or with the hollow profile, for example, by screws or clips.

The closure elements may instead non-releasably connected with each other, for example, by welding or adhesion. Advantageously, the profile wall of the hollow profile and/or of the closure elements has a thickness of at least about 5 mm. Advantageously, provision is made for a pressure equalization of the resonator inner chamber with the atmosphere.

In certain embodiments, the microwave resonator may be fixed to the textile machine such that stresses are equalized. Advantageously, the microwave resonator is arranged in a protective housing. Advantageously, a reference resonator and the measuring resonator are accommodated in an additional, closed housing and for temperature equalization are continuously flushed with air from the outside, which is either fed in from the outside or circulated in a closed circuit. Advantageously, air flows through the resonator for a uniform distribution of the inner climate conditions. Advantageously, the air inside the resonator is exchanged or circulated. Advantageously, the air inside the resonators is continuously exchangeable in the closed circuit between the reference resonator and the measuring resonator. Advantageously, the air inside the resonators is continuously exchangeable with the air in the closed outer housing in the closed circuit between the reference resonator and the measuring resonator. Advantageously, a constant temperature equalization is effected between the reference resonator and the measuring resonator, for example, by heat conducting plates, by air circulation, temperature adjustment etc. In practice it may be possible, by tilting the resonator, for the effect of the anisotropic dielectric constant of certain materials to be reduced.

The measuring resonator and/or the reference resonator may each be a single-cell cavity resonator. In certain embodiments, the measuring resonator may be a multi-cell cavity resonator, for example, a four-cell cavity resonator. The multi-cell cavity cylinder then advantageously has a number of through-openings connected by a tubular element corresponding to the number of cells. Advantageously, two strands of fibres, for example, textile fibre slivers, are conveyable side by side through each through-opening and through each tubular element. In some embodiments, the measuring resonator on the one hand and the reference resonator on the other hand may be two independently separate components. In other embodiments, the measuring resonator and the reference resonator may be a one-piece component, in which a partition wall is arranged to separate the measuring resonator and the reference resonator.

The microwave measuring arrangement of the invention may be used, for example, for control and/or regulation of a processing device for at least one textile fibre sliver. By way of illustration, the microwave measuring arrangement may be arranged at the delivery end of a card. In another illustrative example, at least one microwave measuring arrangement is arranged at the feed end and/or at the delivery end of the drawing system of a draw frame. Advantageously, the drawing system is a card drawing system at the delivery end of a card. The textile fibre sliver may be, for example, a card sliver or a draw frame sliver.

The microwave measuring arrangement may be arranged on a combing machine. The microwave measuring arrangement may be arranged on a combing room preparatory machine.

Advantageously, the microwave measuring arrangement is connected to an electronic control and regulating device, for example, a machine control and regulating device. Preferably, at least one actuator, for example, a variable speed drive motor for altering the thickness of the fibre sliver is connected to the control and regulating device. Preferably, an indicating device, for example, display screen, printer or the like, for displaying the thickness of the fibre sliver is connected to the control and regulating device.

The microwave measuring arrangement may advantageously be used to monitor the thickness of a sliver produced on a card or draw frame.

The invention also provides a microwave resonator for or on a textile machine, especially a card, draw frame, combing machine or the like, for attachment to a measuring device for measuring the mass and/or moisture content of textile fibre material conveyable continuously through a resonator chamber, in which a housing with wall elements is present, wherein through-openings in spaced wall elements lying opposite one another are coaxially connected by a tubular element and the interior space of the housing is hollow, characterised in that the housing comprises a hollow profile with profile walls, in which at least one tubular element is present, which connects through openings in opposite profile walls of the hollow profile with each other.

BRIEF DESCRIPTION OF THE DRAWINGS

FIGS. 5a, 5b show schematically in section a one-piece glass tube with funnel, which has a relatively wide (FIG. 5a) and a relatively narrow (FIG. 5b) internal diameter;

FIG. 6 shows schematically two components comprising a glass tube and a funnel with rubber ring;

FIG. 7 is a perspective view of a closure element with a shoulder;

DETAILED DESCRIPTION OF CERTAIN PREFERRED EMBODIMENTS

Figure 1A:
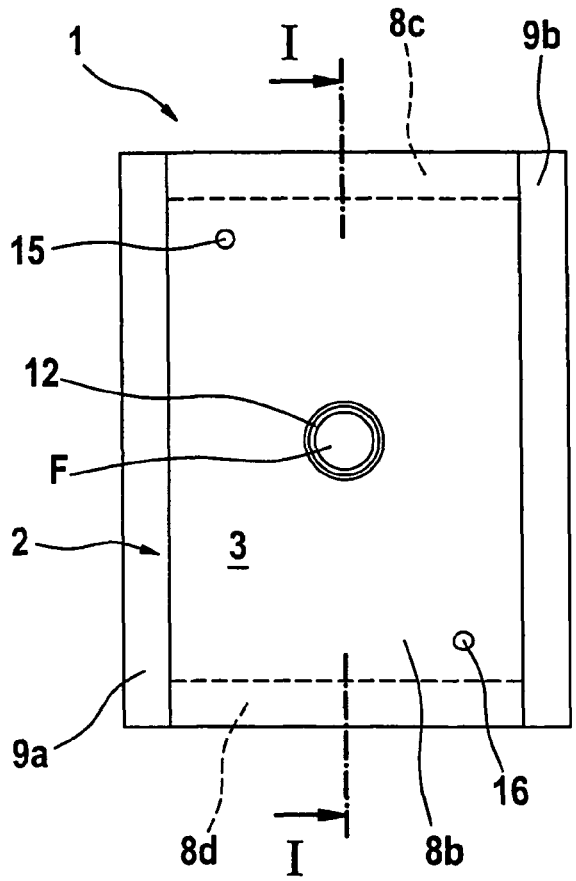
FIGS. 1a, 1b, 1c are sectional views of an embodiment of a microwave resonator according to the invention, in front view (FIG. 1a), side view (FIG. 1b) and plan view (FIG. 1c)
Figure 1B:
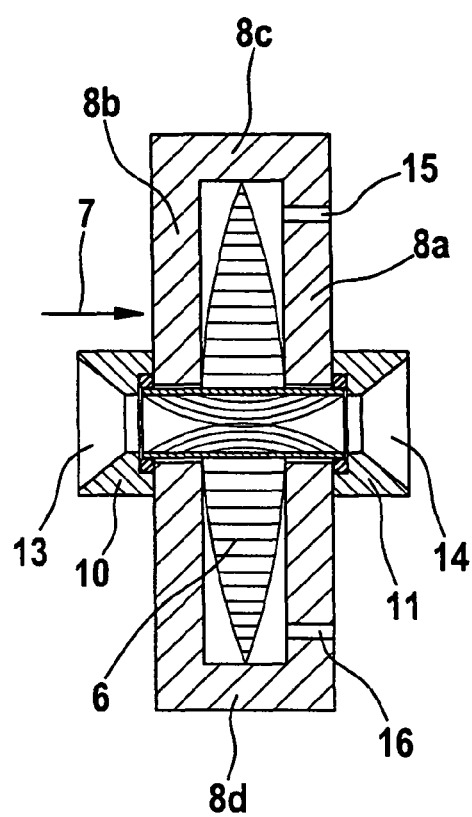
Figure 1C:
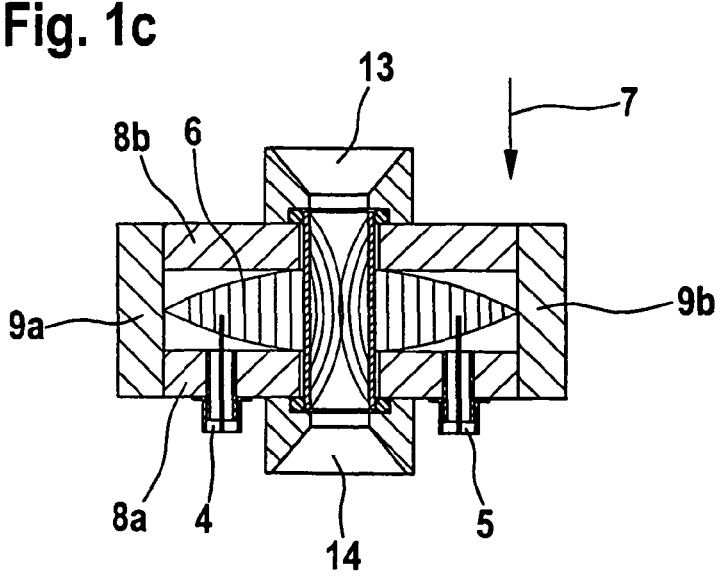

With reference to FIGS. 1a to 1c, there is shown a first illustrative embodiment of microwave resonator 1 (high-frequency resonator arrangement) according to the invention, which comprises a resonator within a housing 2, illustrated in section. The housing is of cuboidal construction, has a cavity 3 in its interior space and consists of electrically conducting material, such as aluminum. Known coaxial cables 4 and 5 respectively are used to inject an electromagnetic microwave signal from a generator and to extract a microwave signal (microwave field) to an evaluating device. The reference numeral 6 denotes the electrical field in the closed cavity resonator. The reference numeral 7 denotes the running direction of the fibre material F, for example, a textile fibre sliver.

The housing 2 comprises a hollow profile 8, in the example an aluminum extrusion-moulded hollow profile (precision profile), the rectangular cross-sectional shape of which encloses the cavity 3 of rectangular cross-section. The seamless hollow profile 8 has four profile walls 8a to 8d, a front wall 8a, a rear wall 8b, a top wall 8c and a bottom wall 8d. A respective panel 9a, 9b is mounted, for example, using screws, at the two end faces of the hollow profile 8 as a closure element. The hollow profile 8 has an inlet opening 10 and an outlet opening 11. In order to detect its dry mass and/or moist mass and/or overall mass, the textile fibre sliver F is guided in a tubular guide 12 of electrically non-conducting material, for example, quartz, through the hollow profile 8 of the housing 2, corresponding to the arrow 7. Dust or the like is prevented by this measure from entering the cavity 3 (resonator chamber), and causing interference. A funnel-like inlet element 13 and a funnel like outlet element 14 of conductive material, such as metal, prevent emission of the high frequency field to a disruptive extent through the inlet and outlet openings 10 and 11 respectively of the hollow profile 8. In addition, the conical shaping of the funnel-shaped elements 13 and 14 assist guidance of the fibre sliver F through the inlet opening 10 and outlet opening 11.

Two through-bores are present, one as inlet opening 10 through the profile wall 8b and one as outlet opening through the profile wall 8a. Furthermore, a glass tube 12 is provided as the tubular element that coaxially connects the inlet opening 10 with the outlet opening 11 in the opposite profile walls 8a, 8b of the hollow profile 8.

In the profile wall 8b, slightly spaced from the covering panel 9a, and in the profile wall 8a close to the covering panel 9b, there is a small continuous bore 15 respectively 16 of, for example, 3 mm diameter, which creates an air exchange between the interior space 3 and the atmosphere.

By way of the coaxial cable 4, microwave signals emitted by a generator, preferably in the GHz range, for example at frequencies of about 6 GHz, are fed into the resonator. A high-frequency signal influenced by the textile fibre sliver F for detecting a resonant frequency shift and attenuation compared with a signal uninfluenced by the textile fibre sliver F can be extracted from the resonator and fed via the coaxial cable 5 to an evaluating device (see FIG. 8).

Figure 2:
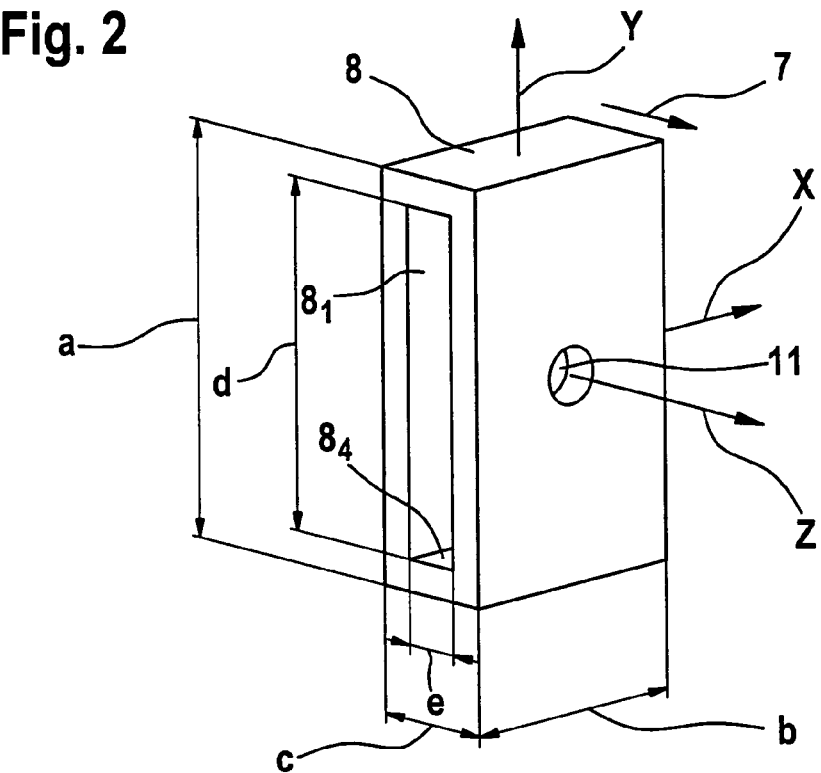
FIG. 2 is a perspective view of a hollow profile of rectangular cross-section.

In FIG. 2, there is shown one form of hollow profile suitable for use in the apparatus of the invention. The hollow profile is in the form of an extrusion-moulded hollow profile, for example, of $AlMgSiO_5$, the cross-sectional shape of which encloses a closed cavity. The hollow profile 8 is in the form of a cuboid with external dimensions height=a, width=b (length) and depth=c. The interior space 3 of the hollow profile 8 has a rectangular cross-sectional shape, is hollow and has the internal dimensions height=d, width=b (length) and depth=e. The hollow profile 8 is produced by cutting it off, for example, by sawing or laser cutting, in a length=b from a semi-finished extrusion-moulded hollow profile (not shown). The hollow profile 8 in the exemplary embodiment is in one piece. The profile walls 8a to 8d have four internal wall areas, a front wall area $8_1$, a rear wall area $8_2$ (FIG. 3), a top wall area $8_3$, (FIG. 3) and a bottom wall area $8_4$. The total inner wall area $8_1$ to $8_4$ is closed and smooth. The hollow profile 8 is essentially in the form of a rectangular pipe. The inner wall areas $8_1$ to $8_4$ are each rectangular. The edges of the right-angled (abutting) inner wall areas $8_1$ to $8_4$ are rounded. In view of the rectangular cross-section of the interior space 3, the long sides of the rectangle are arranged perpendicular to the axis X of the tubular element 12 (see FIG. 1) and to the conveying direction 7 of the textile fibre sliver F. The parallel wall areas $8_1$ and $8_2$ are arranged perpendicular to the conveying direction of the textile fibre material F and to the axis X of the tubular element 12. The short sides of the rectangle are arranged parallel to the axis X of the tubular element 12 (see FIG. 1) and to the conveying direction of the textile fibre material F. The parallel wall areas $8_3$ and $8_4$ are arranged parallel to the conveying direction 7 of the textile fibre material F and to the axis X of the tubular element 12. The dimensions of the cavity 3 are advantageously height d of about 110 to 130 mm and depth e of about 12 to 18 mm. The width b depends on the whether a single-cell resonator (FIG. 1) or a multi-cell resonator (FIG. 4) is present and on the propagation of the resonance field 6 in the resonator chamber 3. The reference numeral 11 denotes the outlet opening. X denotes the axis of the hollow profile 8 in the direction of the depth c and e respectively, Y denotes the axis of the hollow profile 8 in the direction of the height a and d respectively and Z denotes the axis of the hollow profile 8 in the direction of the width b (length).

Figure 3:
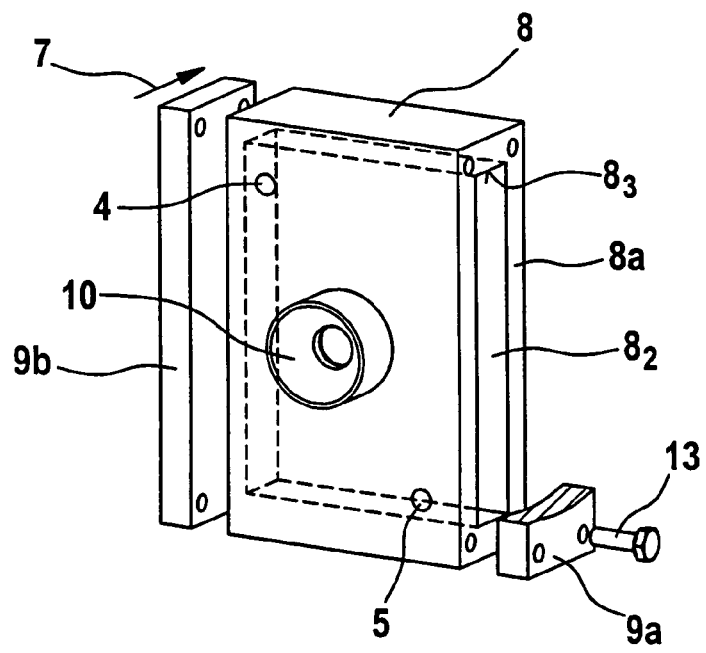
FIG. 3 is a perspective view of the housing with a hollow profile and two closure elements arranged at the end faces, as well as the inlet opening in a profile wall and two antenna connections in a profile wall.

In the embodiment of FIG. 3, the two open end faces of the hollow profile 8 can be closed off by a respective closure panel 9a, 9b. Screws 13 (only one of which is shown) are provided for that purpose, which engage through bores in the closure panels 9a, 9b into threaded bores provided on the end faces of the hollow profile 8 in the profile walls 8a to 8d. The closure panels 9a, 9b consist of aluminum in the example. The closure panels 9a, 9b must be secured with firm contact pressure, providing good conduction, to the hollow profile 8, in order to avoid an interruption in the current flow. The reference numeral 10 denotes the inlet opening.

Figure 4A:
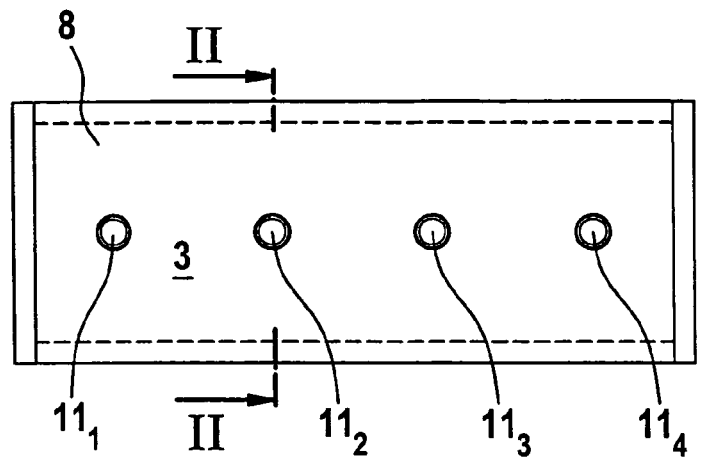
FIGS. 4a, 4b, 4c are sectional views of another embodiment of a microwave resonator according to the invention, in the form of a four-cell cavity resonator, in front view (FIG. 4a), side view (FIG. 4b) and plan view (FIG. 4c)
Figure 4B:
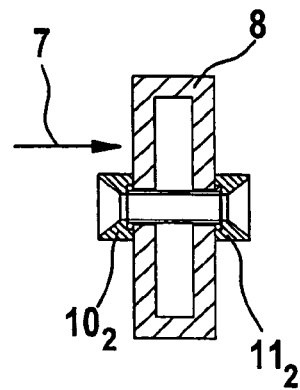
Figure 4C:
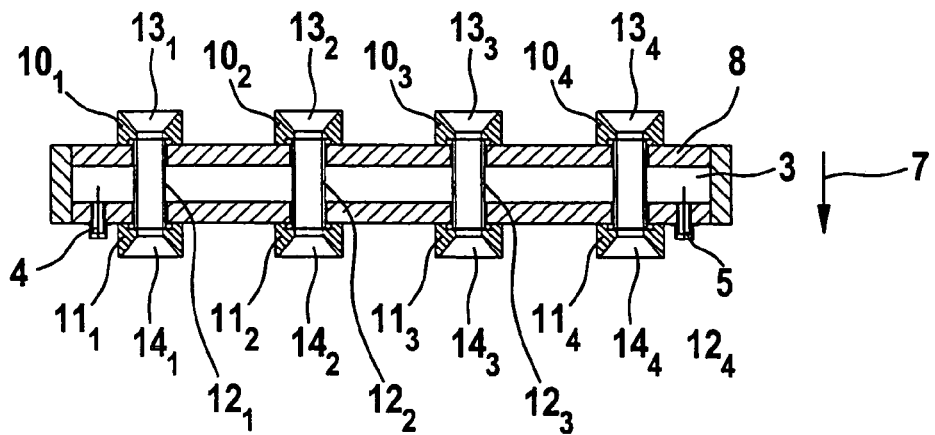

In the embodiment of FIGS. 4a to 4c, a four-cell cavity resonator is provided, comprising a butt-mounted arrangement of four individual resonators. In the interior space 3 there are no partition walls or the like between the resonators. A resonator field builds up in the interior space 3. The electromagnetic wave couples up to the transmitting antenna 4 and to the receiving antenna 5 at the two ends of the resonator. The hollow profile 8 is an aluminum extrusion- moulded hollow profile. There are eight through-bores present, four as inlet openings $10_1$ to $10_4$ through the profile wall 8b and four as outlet openings $11_1$ to $11_4$ through the profile wall 8a. Furthermore, four quartz glass tubes $12_1$ to $12_4$ are provided as tubular elements, which coaxially connect the inlet openings $10_1$ to $10_4$ with respective outlet openings $11_1$ to $11_4$, the openings being arranged in opposite profile walls 8b, 8a respectively of the hollow profile 8. Funnel-like elements $13_1$ to $13_4$ and $14_1$ to $14_4$ are furthermore associated with the quartz glass tubes $12_1$ to $12_4$.

Figure 4D:
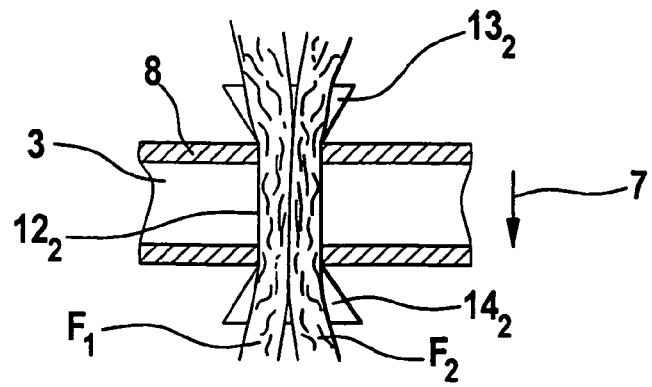
FIG. 4d shows a cut-out from FIG. 4c with two fibre slivers being fed through a glass tube.

FIG. 4d shows a cut-out from FIG. 4c with two fibre slivers $F_1$, $F_2$ conveyed side by side through a glass tube $12_2$. This construction has the advantage that, if a fibre sliver $F_1$ or $F_2$ tears before the inlet opening $10_2$, the end of the torn fibre sliver is attached to the other, still continuous, fibre sliver, for example, by rubbing, and the torn and the continuous fibre sliver are conveyed together through the glass tube $12_2$. This does away with the time-consuming threading of the torn fibre sliver through the glass tube $12_2$.

In the embodiment of FIGS. 5a, 5b, the glass tube 12 has at one end a funnel-form extension $12^I$, whereby a one-piece component is formed. The glass tube 12 can be pushed right through the metal, funnel-like element 13 and through the inlet opening 10 and the outlet opening 11 (see FIG. 1b). The outer surface of the extension $12^I$ rests against the inner surface of the funnel-like element 13. The outer diameter f of the glass tube 12 is the same in the embodiment shown in FIGS. 5a and 5b. However, the inner diameter g in FIG. 5a is larger than the inner diameter g in FIG. 5b. By exchanging the glass tubes 12, fibre slivers F of different diameter can advantageously be processed and measured.

In the embodiment of FIG. 6, the inlet opening 10 and the outlet opening 11 through which the glass tube 12 is pushed are arranged in the profile wall $8b$ and in the profile wall $8a$ respectively. The diameter i of the inlet opening 10 and the outlet opening 11 is larger than the outer diameter f of the glass tube 12 such that a gap is present. The funnel-like element 14 is fixed to the outer surface of the profile wall $8a$ by a screw 17. The funnel-like element 14 is manufactured from a metal cylinder, the conically tapering funnel chamber $14^I$ being shaped therefrom at one end and a cylindrical aperture $14^{III}$ being shaped therein at the other end, each being connected to the other by a continuous opening $14^{II}$. A rubber ring 18 is arranged between the outer surface of the glass tube 12 and the circular inner wall area of the aperture $14^{II}$. In this way, the spacing between glass tube 12 and outlet opening 11 is ensured. In addition, the resilient rubber ring 18 prevents transference of force from the glass tube 12 to the profile wall $8a$. For the sake of simplicity, an (existing) corresponding connection between the funnel-form element 13 and the inlet opening 10 at the other end of the glass tube 12 (see FIG. $1b$) at a rubber ring 19 is not shown.

In the embodiment of FIG. 7, on the inner wall area $9^I$ of the closure panel $9a$ there is a shoulder-like raised moulding $9^{II}$, which is of rectangular construction and has a width e and a length d. In this way, the raised moulding $9^{II}$ is able to engage with a positive connection in the end-face, rectangular hollow opening of the hollow profile 8 (for example, the hollow profile of FIG. 2).

Figure 8:
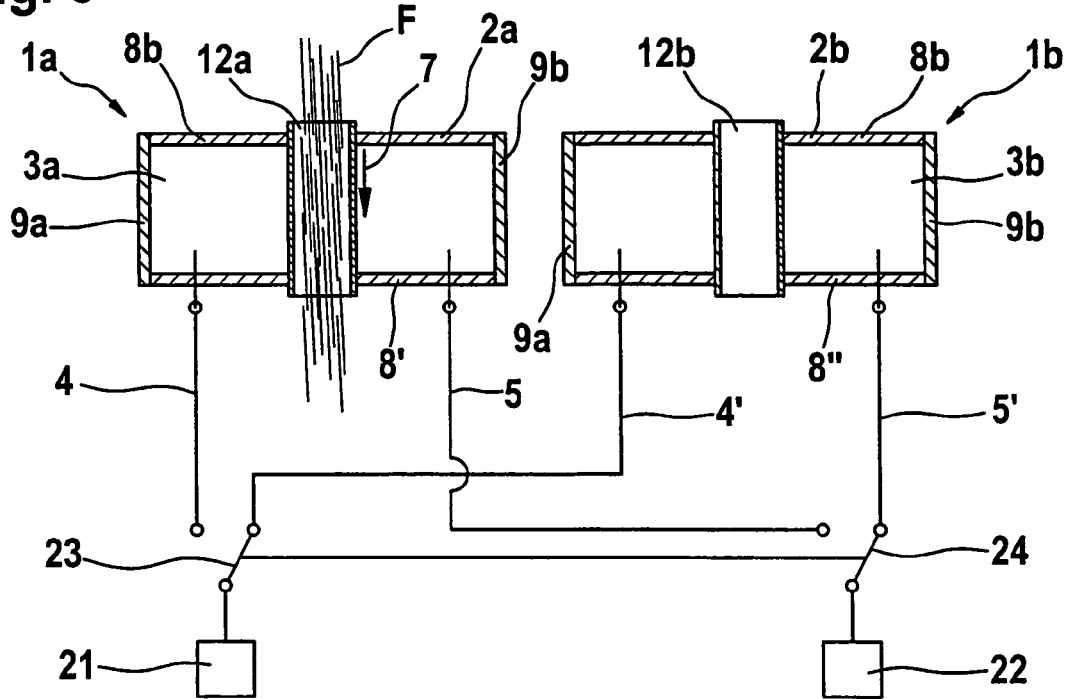
FIG. 8 is a cross-sectional view of a microwave measuring arrangement with spatially separated measuring resonator and reference resonator.
Figure 9:
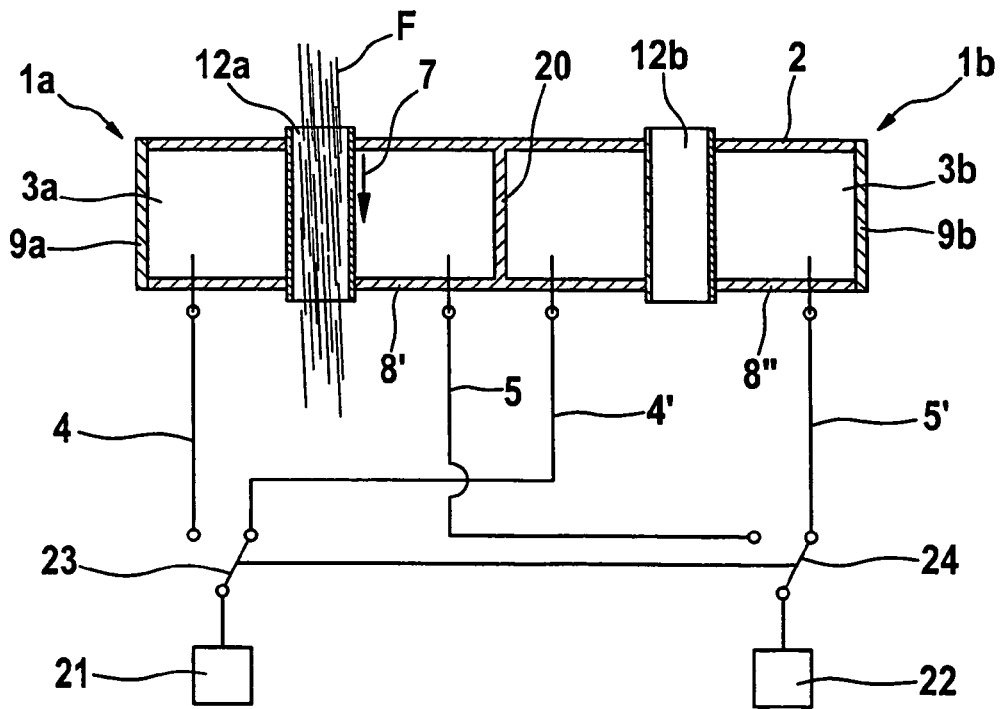
FIG. 9 is a cross-sectional view of a microwave measuring arrangement in which the measuring and reference resonators are adjacent to each other and form a modular unit.

In the embodiment of FIGS. 8 and 9 show a measuring arrangement with a measuring resonator $1a$ and a reference resonator $1b$, FIG. 8 showing a spaced measuring arrangement and FIG. 9 showing a structurally unitary measuring arrangement. According to FIG. 9, a metallic partition wall 20 is provided between the resonator chambers $3a$, $3b$. The microwave resonator 1 according to the invention may be used both as a measuring resonator $1a$ and as a reference resonator $1b$. The measuring resonator $1a$ comprises a hollow profile $8^I$ and the reference resonator $1b$ comprise a hollow profile $8^{II}$.

The fibre sliver F is guided through two openings through the resonator chamber $3a$ of the measuring resonator $1a$. Microwaves are generated by means of suitable devices 21 (microwave generators), and fed into the resonator $1a$ via a connection 4. At a specific frequency, standing waves are induced in the resonator $1a$. Microwaves enter the interior space of the glass tube $12a$ and interact with the fibre sliver F located therein. The microwaves are output via a connection 5 and passed to a downstream evaluating device 22. The reference resonator $1b$ is arranged directly adjacent to the measuring resonator 1. Microwaves that are preferably tapped off from the infeed 21 by means of the switch 23 are injected into and fed out of the reference resonator $1b$. The microwaves are passed to the evaluating unit 22 via the switch 24.

The switching frequency of the switches 23 and 24 can be as high as desired. Because the reference resonator $1b$ and the measuring resonator $1a$ are of the same construction, the conditions obtaining in the two resonators $1a$, $1b$ are the same at all times, e.g. the temperature distribution is approximately the same. For measurement, the frequency of the field in the resonator 1 is driven through a range that contains a specific, isolated resonance. The range to be passed through depends inter alia on the product in question and on the humidity and temperature values occurring in practice (owing to the magnitude of the resonance shift consequent thereon). From the starting signal, the resonant frequency $f_1$ and the half-value width $\Gamma_1$ of the measured resonance are determined in an evaluating unit. Such a measuring and evaluating cycle can take place in a fraction of a second. The measurements in the measuring resonator $1a$ and in the reference resonator $1b$ are carried out preferably at approximately comparable frequencies in order to avoid dispersion influences. The reference resonator $1b$ is accordingly preferably dimensioned so that the frequency ranges to be passed through in the case of the measuring resonator $1a$ and the reference resonator $1b$ have a mean spacing of less than 1 GHz, preferably less than 100 MHz, additionally preferably less than 10 MHz. The measurements take place preferably in the frequency range from 0.1 to 20 GHz, additionally preferably 2 to 3 GHz, additionally preferably 2.4 to 2.5 GHz.

Figure 10:
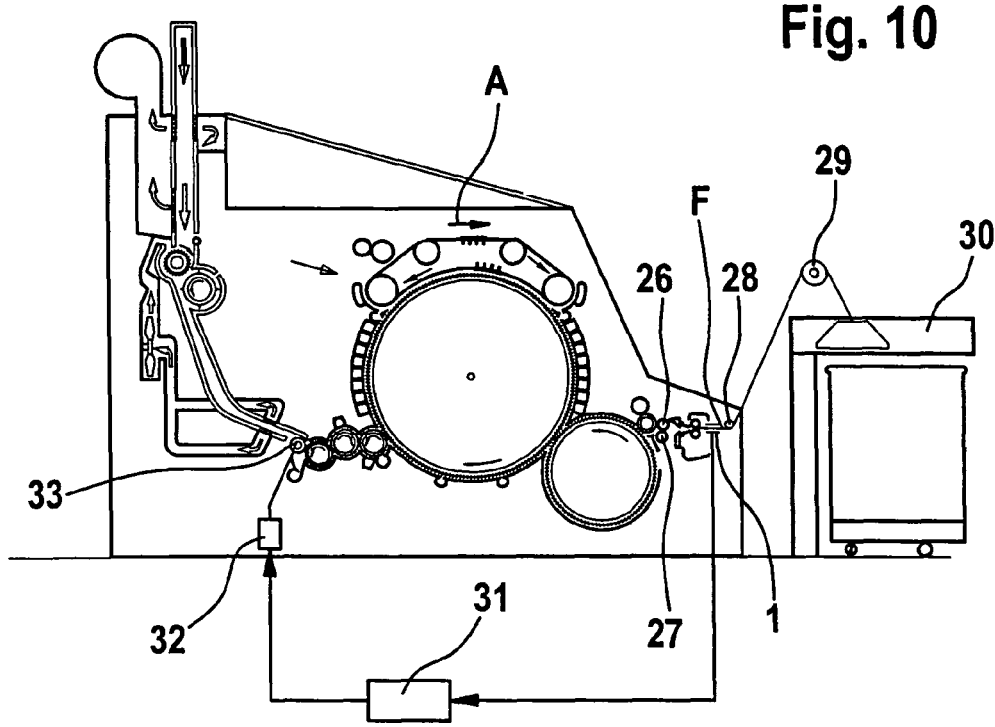
FIG. 10 is a diagrammatic side view of a card with the microwave measuring arrangement using at least one microwave resonator.

FIG. 10 shows a carding machine 25, for example, a card TC 03 (trade mark) made by Trützschler GmbH & Co. KG of Mönchengladbach, Germany, as illustrated and described in DE-A 10 2005 009 159. The take-off rollers 26, 27 draw off a card sliver F, which passes over guide rollers 28, 29 to the can coiler 30 and from there is laid in the can. The card includes a microwave resonator 1 according to the invention arranged between the take-off rollers 26, 27 and the guide roller 28. The microwave measuring arrangement 1 is connected to an electronic control and regulating device 31, for example, a microcomputer, which alters the rotational speed of the feed roller 33 by way of a variable speed drive motor 32. In this way, the density of the card sliver F, which can leave the take-off rollers at high speed, for example, 200 m/min or more, is adjusted. The letter A denotes the direction of working.

Figure 11:
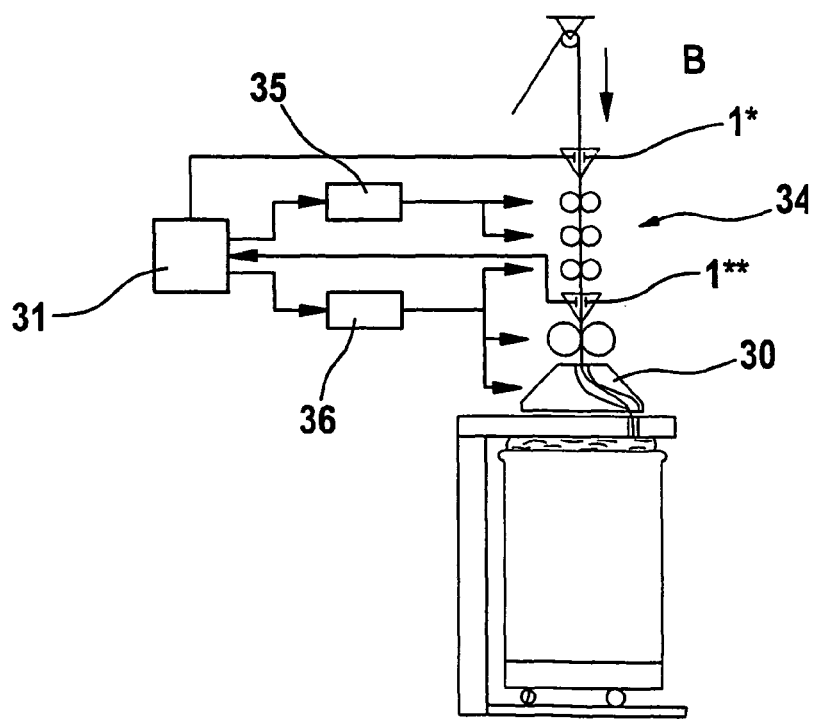
FIG. 11 shows a fibre sliver coiler device with an integrated autoleveller drawing system with a microwave measuring arrangement using at least one microwave resonator.
Figure 13:
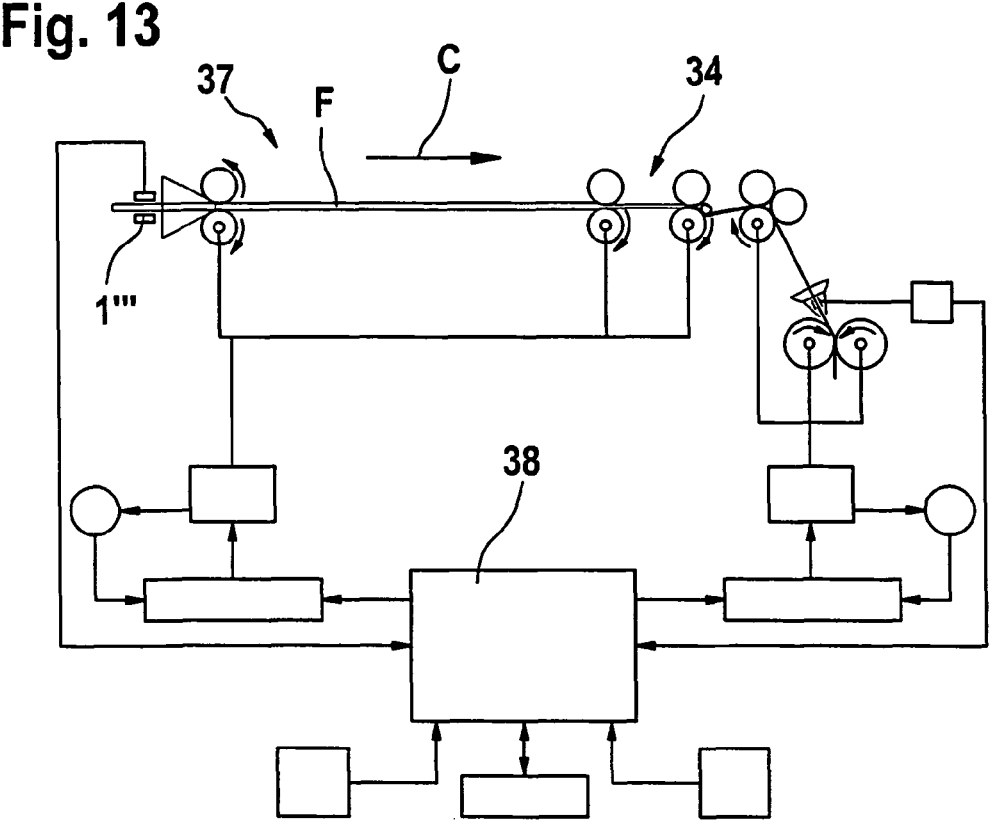
FIG. 13 shows schematically in side view an autoleveller draw frame having a microwave measuring arrangement at the feed end and delivery end, using at least one microwave resonator.

Referring to FIG. 11, a drawing system 34, which is similar in general construction to the drawing system shown in FIG. 13, is arranged above the can coiler 30; reference will be made to the description of the drawing system of FIG. 13. At the feed end and delivery end of the drawing system 34 there is a respective microwave measuring arrangement $1^*$ and $1^{**}$, which are connected to the electronic control and regulating device 31, which is furthermore connected to drive motors 31, 32 for the drawing system 34 and to a drive motor for the can turntable. FIG. 11 shows an integrated card draw frame (IDF) according to DE-A-10 2005 009 159. The letter B denotes the direction of working.

Figure 12:
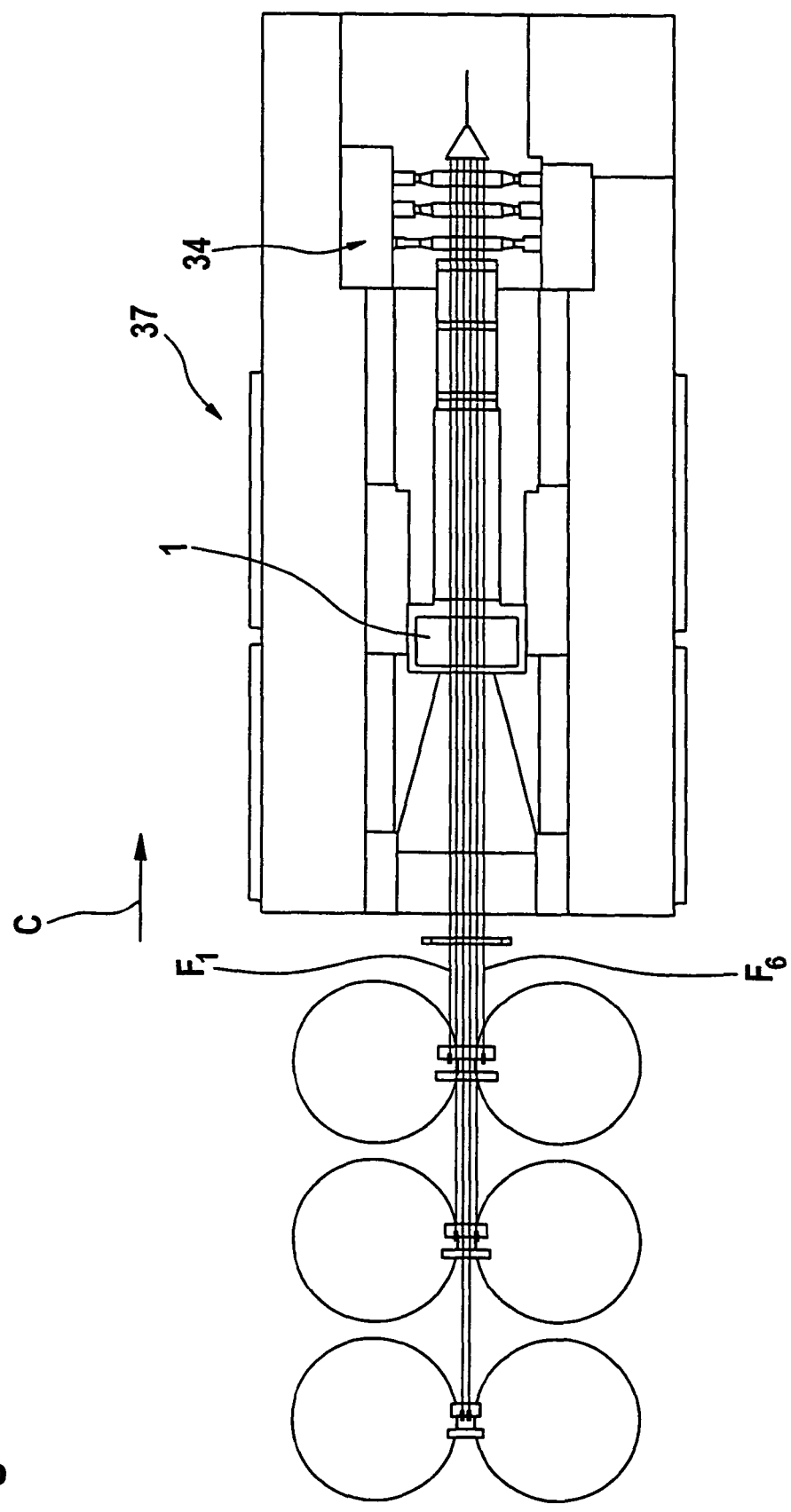
FIG. 12 is a plan view of a draw frame with fibre slivers running substantially rectilinearly and parallel and with at least one microwave resonator.

FIG. 12 is a plan view of a draw frame 37, for example, a draw frame made by Trützschler GmbH & Co. KG, with fibre slivers $F_1$ to $F_6$ running substantially rectilinearly and parallel to one another which, coming from spinning cans and a feed table situated upstream, pass through a multi-cell microwave resonator 1 according to the invention, subsequently through a drawing system 34 located downstream (see FIG. 13) and are fed as a drawn fibre sliver to subsequent processing stations. Owing to the fact that from the feed table as far as the web guide means the fibre slivers $F_1$ to $F_6$ are continuously present in the form of single or double slivers (see FIG. $4d$), which maintain their running direction, and owing to the spaced arrangement of the through-openings $11_1$ to $11_4$, undesirable structure changes, especially loss due to friction, are avoided. The fibre slivers $F_1$ to $F_6$ pass through the feed table, the microwave resonator 1 and the drawing system 34 substantially parallel and with their direction virtually unaffected, thus making a substantially higher production speed possible. In particular, a number of components for direction changes and the like can be dispensed with, which in terms of construction and assembly represents a considerable simplification. The substantially straight alignment of the fibre slivers $F_1$ to $F_6$ in the running direction, combined with continuous retention of the form of the fibre slivers $F_1$ to $F_6$ and the spaced arrangement of the through-openings $11_1$ to $11_4$, bring about the advantages in respect of design and function of the features according to the invention. The through-openings $11_1$ to $11_4$ can instead be spaced by arranging (in manner not shown) a plurality of single-cell resonators 1 side by side.

FIG. 13 shows a draw frame 37, for example, a draw frame TD 03 (trade mark) made by Trützschler GmbH & Co. KG, as shown and described in DE-A-10 2005 009 159. The draw frame 37 has a drawing system 34, upstream of which is a drawing system feed and downstream of which is a drawing system outlet. The fibre slivers enter the sliver guide from cans (not shown) and, drawn by the take-off rollers, are transported to the drawing system 34. The drawing system 34 is designed as a 4-over-3 drawing system, that is, it consists of three bottom rollers I, II, III (I being the bottom delivery roller, II being the bottom middle roller and III being the bottom feed roller) and four top rollers. Drafting of the composite fibre sliver, comprising several fibre slivers, takes place in the drawing system 34. The draft is made up from the preliminary draft and the main draft. The roller pairs form a preliminary drafting zone and a main drafting zone. The drawn fibre slivers reach a web guide at the outlet of the drawing system and are drawn by means of the take-off rollers through a sliver funnel, in which they are condensed to a fibre sliver, which is subsequently deposited in a can. The letter C denotes the working direction. The take-off rollers, the bottom feed roller III and the middle bottom roller II, which are mechanically linked, for example, by way of toothed belts, are driven by the variable speed motor, it being possible to pre-set a desired value. At the inlet to the drawing system, a variable proportional to the density of the fed-in fibre slivers is measured by a microwave resonator $1^{III}$ (feed-side measuring device) according to the invention. At the outlet of the drawing system, the density of the fibre sliver is obtained from a microwave resonator $1^{IV}$ (delivery-side measuring device) according to the invention associated with the sliver funnel. A central computer unit 38 (control and regulating device), e.g. a microcomputer with microprocessor, determines a setting of the regulated variable for the variable speed motor. The measured variables of the two measuring devices $1^{III}$ and $1^{IV}$ are sent during the drawing process to the central computer unit 38. From the measured variables of the feed-side measuring device $1^{III}$ and from the desired value for the density of the emerging fibre sliver, the adjustment value for the variable speed motor is determined in the central computer unit 38. The measured variables of the delivery-side measuring device $1^{IV}$ are used to monitor the emerging fibre sliver (monitoring of delivered sliver). By means of this control system, fluctuations in the density of the fed-in fibre slivers F can be compensated by corresponding adjustments to the drafting process and the fibre slivers $F_1$ to $F_6$ can be evened out. The letter C denotes the direction of working.

Figure 14:
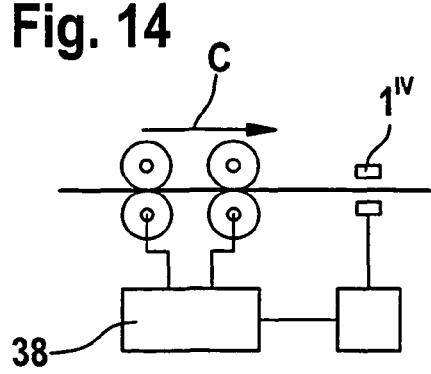
FIG. 14 shows an autoleveller draw frame with a closed control loop (regulation) and at least one microwave resonator.
Figure 15:
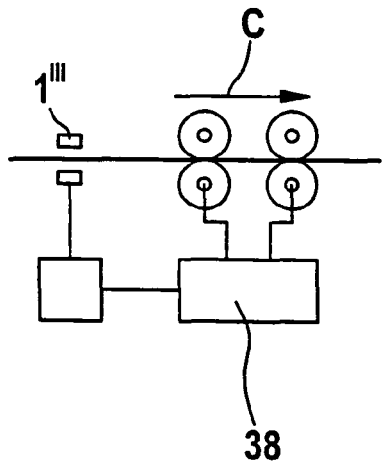
FIG. 15 shows an autoleveller draw frame with an open control loop (control), and at least one microwave resonator.
Figure 16:
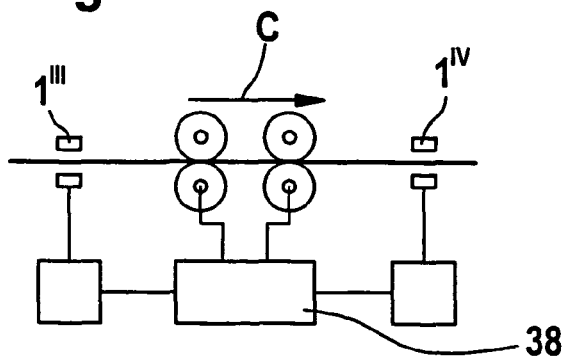
FIG. 16 shows an autoleveller draw frame with a combination of an open and a closed control loop (reference variable input) and at least one microwave resonator.

FIGS. 14, 15 and 16 show alternative basic layouts of the drawing system of a draw frame with different constructions for the adjustment of the fibre sliver density. FIG. 14 shows an embodiment with a closed control loop, in which the microwave measuring arrangement is arranged at the delivery end of the drawing system. The fibre material leaving the drawing system passes through the measuring arrangement, the output signal of which is compared in the control electronics with a desired value and is converted so that a corresponding control signal is supplied to an actuator (variable speed motor) for the roller II. The output signal corresponding to the density of the emerging fibre material thus influences the speed ratio of the drafting roller pairs in the sense that the fibre material is evened out. FIG. 15 shows an embodiment with an open control loop (control). Here, the microwave measuring arrangement is located in the region in which the fibre material approaches the drawing system, measures the density of the fibre material and the corresponding measuring signal is converted in the control electronics 38 into a control signal, which is supplied to an actuator (variable speed motor) for the roller II. Allowances are made electronically for the time taken by the fibre material to run from the measuring arrangement $1^{III}$ to the drawing system. FIG. 16 shows an embodiment with a combination of an open and a closed control loop, in which the measuring signals of the measuring arrangement $1^{IV}$ are superimposed on the measuring signals of the measuring arrangement $1^{III}$.

On a production machine, for example, a card 25 and draw frame 32, for the control and/or adjustment and also for monitoring the uniformity of the fibre slivers produced, compensation of environmental influences and disturbance variables can be effected by the reference resonator $1b$, preferably during regular pauses in production and/or during machine stoppages, for example, can changes, in which measurements with the measuring resonator $1a$ are not required. The reference measurement in the reference resonator $1b$ can be effected at regular or irregular intervals. It may be sufficient for a measurement to be carried out in reference resonator $1b$ after several minutes, preferably at the latest after a few hours, if environmental influences or disturbance variables have only a correspondingly slow effect. The efficiency of the machine is not affected thereby. When the change-over of the switches 23 and 24 and the stabilization of the electrical field in the resonators $1a$ and $1b$ is effected within a short time, correction of the microwave measuring arrangement can be effected within a correspondingly short time. In this way, environmental influences and disturbance variables can be compensated during ongoing production in a processing machine.

Figure 17:
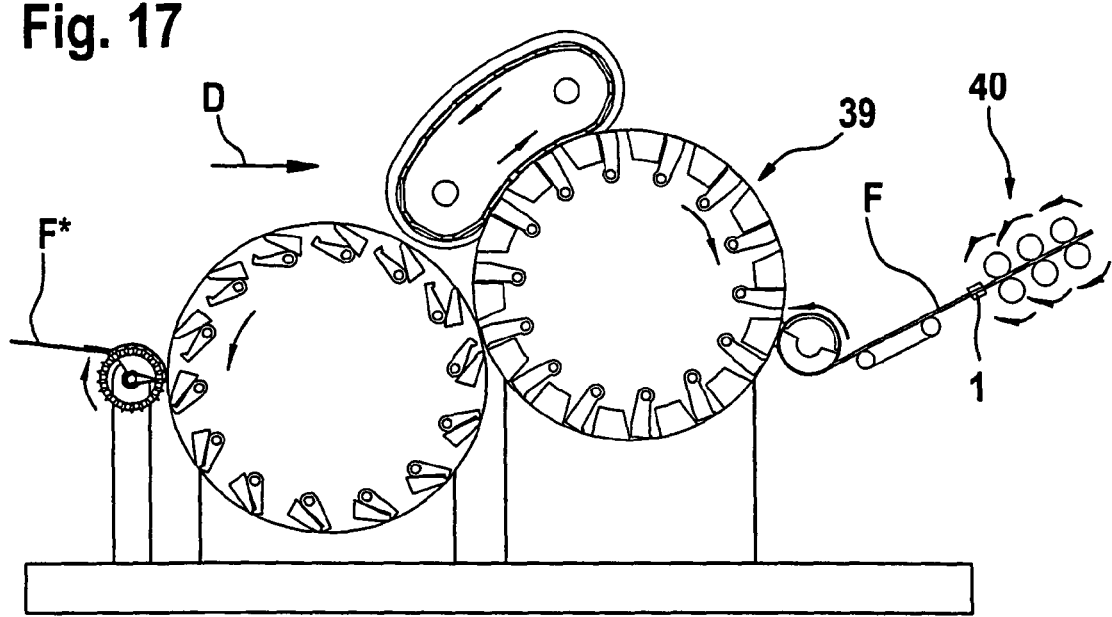
FIG. 17 shows schematically in side view a rotor combing machine having at least one microwave resonator.

FIG. 17 shows a rotor combing machine 39 of the firm Trützschler GmbH & Co. KG in Mönchengladbach. The rotor combing machine 39 is arranged downstream of a drawing system 40, which draws and evens out the drawn combed sliver F. The microwave resonator 1 according to the invention is arranged between the rotor combing machine 39 and the drawing system 40. The letter D denotes the direction of working.

Figure 18:
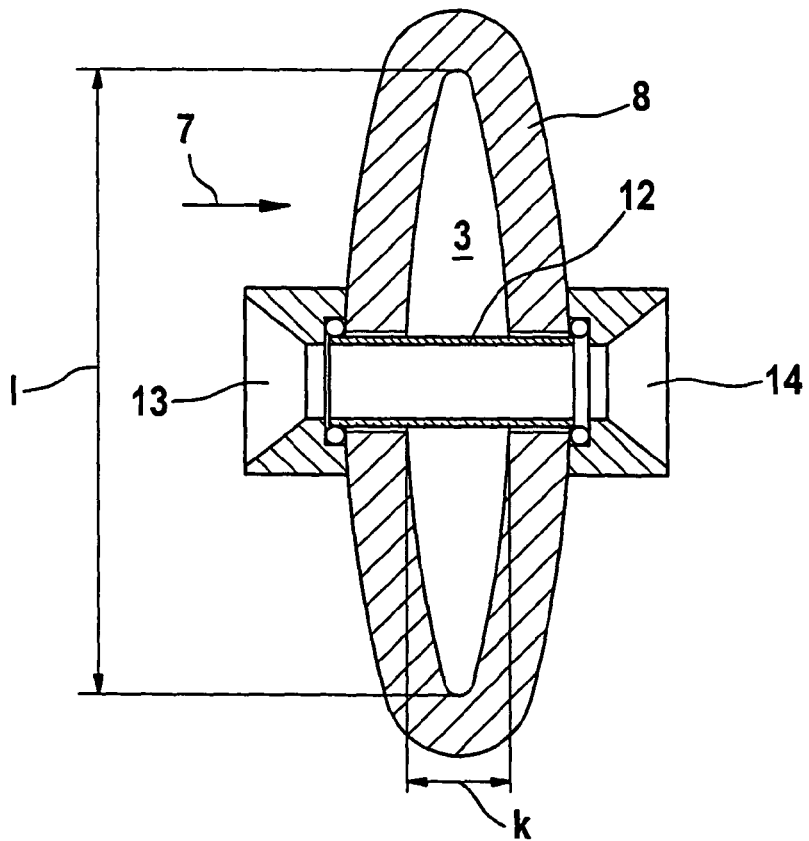
FIG. 18 shows a hollow profile having an oval cross-section.

In the embodiment of FIG. 18, a hollow profile 8 having an oval, for example, elliptical, cross-section is provided. Notably the cavity 3 has an oval, for example, elliptical cross-section. In the case of the cross-section of the cavity 3, the short axis k is arranged parallel and the long axis 1 is arranged perpendicular to the conveying direction 7 of the textile fibre material F. The hollow profile 8 can alternatively be in the form of a cuboid (not shown), which has a cavity 3 with an oval cross-section.

"Resonator" relates to a spatial region in which a standing microwave field is able to propagate. The resonator can be a closed or a substantially closed cavity resonator.

Air enters respectively exits through the inlet opening 10 and the outlet opening 11 of the reference resonator $1b$.

Although the foregoing invention has been described in detail by way of illustration and example for purposes of understanding, it will be obvious that changes and modifications may be practiced within the scope of the appended claims.

What is claimed is:

1. A microwave resonator for or on a textile machine for attachment to a measuring device for measuring the mass and/or moisture content of textile fibre material comprising:

a resonator chamber through which textile fibre material is conveyable continuously, having a housing with wall elements including spaced, opposed first and second wall elements;

an inlet through-opening in said first wall element and an outlet through-opening in said second wall element; and at least one tubular element coaxially connecting said inlet and outlet through-openings;

wherein the housing comprises a hollow profile with profile walls of which first and second opposite profile walls of the hollow profile form said first and second wall elements in which said connected through-openings are located;

further wherein the microwave resonator is used for control and/or regulation of a processing device for at least one textile fibre sliver.

2. A microwave resonator according to claim 1, in which the interior space defined by the hollow profile is closable by at least one closure element to form a cavity resonator.

3. A microwave resonator according to claim 1, in which the hollow profile is produced by a method comprising one or more techniques selected from the group consisting of non-machining shaping, plastic deformation, extrusion moulding, drawing, rolling and casting.

4. A microwave resonator according to claim 1, in which the hollow profile comprises a metallic material selected from the group consisting of aluminum, aluminum alloys, copper, steel, and iron-nickel steel (Invar).

5. A microwave resonator according to claim 1, in which the hollow profile is monolithic.

6. A microwave resonator according to claim 1, in which the hollow profile has at least one subsequently machined, joining seam.

7. A microwave resonator according to claim 1, in which the hollow profile is a tubular member having a cross-section configuration adapted circumferentially to enclose a resonator cavity.

8. A microwave resonator according to claim 1, in which the resonator chamber is enclosed on all sides.

9. A microwave resonator according to claim 1, in which the tubular element comprises glass or quartz glass.

10. A microwave resonator according to claim 1, in which the measuring resonator is a multi-cell cavity resonator, in which the multi-cell cavity has a number of pairs of through-openings connected by a tubular element corresponding to the number of cells.

11. A microwave resonator according to claim 1, in which two strands of fibres are conveyable side by side through each through-opening and through each tubular element.

12. A microwave resonator for or on a textile machine for attachment to a measuring device for measuring the mass and/or moisture content of textile fibre material comprising:

a resonator chamber through which textile fibre material is conveyable continuously, having a housing with wall elements including spaced, opposed first and second wall elements;

an inlet through-opening in said first wall element and an outlet through-opening in said second wall element; and at least one tubular element coaxially connecting said inlet and outlet through-openings;

wherein the housing comprises a hollow profile with profile walls of which first and second opposite profile walls of the hollow profile form said first and second wall elements in which said connected through-openings are located;

further wherein the hollow profile is a tubular member having a cross-section configuration adapted circumferentially to enclose a resonator cavity, and the enclosed cavity is of rectangular or oval cross-section and the longer sides of the rectangle or oval run perpendicular to the axis of the tubular element and to the conveying direction of the textile fibre material, the shorter sides of the rectangle or oval running parallel to the axis of the tubular element and to the conveying direction of the textile fibre material.

13. A microwave resonator according to claim 12, in which the ratio of height to depth in the chamber of the resonator is about 1:6 to 10, the chamber having a height of about 110 to 130 mm and a depth of about 12 to 18 mm.

14. A microwave resonator for or on a textile machine for attachment to a measuring device for measuring the mass and/or moisture content of textile fibre material comprising:

a resonator chamber through which textile fibre material is conveyable continuously, having a housing with wall elements including spaced, opposed first and second wall elements;

an inlet through-opening in said first wall element and an outlet through-opening in said second wall element; and at least one tubular element coaxially connecting said inlet and outlet through-openings;

wherein the housing comprises a hollow profile with profile walls of which first and second opposite profile walls of the hollow profile form said first and second wall elements in which said connected through-openings are located, and the resonator chamber is enclosed by an electrically conducting layer or wall.

15. A microwave resonator for or on a textile machine for attachment to a measuring device for measuring the mass and/or moisture content of textile fibre material comprising:

a resonator chamber through which textile fibre material is conveyable continuously, having a housing with wall elements including spaced, opposed first and second wall elements;

an inlet through-opening in said first wall element and an outlet through-opening in said second wall element; and at least one tubular element coaxially connecting said inlet and outlet through-openings;

wherein the housing comprises a hollow profile with profile walls of which first and second opposite profile walls of the hollow profile form said first and second wall elements in which said connected through-openings are located, and the inner wall areas of the hollow profile are provided with an electrically conducting layer and/or are coated for protection against oxidation.

16. A microwave resonator for or on a textile machine for attachment to a measuring device for measuring the mass and/or moisture content of textile fibre material comprising:

a resonator chamber through which textile fibre material is conveyable continuously, having a housing with wall elements including spaced, opposed first and second wall elements;

an inlet through-opening in said first wall element and an outlet through-opening in said second wall element; and at least one tubular element coaxially connecting said inlet and outlet through-openings;

wherein the housing comprises a hollow profile with profile walls of which first and second opposite profile walls of the hollow profile form said first and second wall elements in which said connected through-openings are located, and the tubular element shuts off regions of the resonator chamber and is adapted to guide the textile fibre material through the resonator chamber.

17. A microwave resonator for or on a textile machine for attachment to a measuring device for measuring the mass and/or moisture content of textile fibre material comprising:
- a resonator chamber through which textile fibre material is conveyable continuously, having a housing with wall elements including spaced, opposed first and second wall elements;
- an inlet through-opening in said first wall element and an outlet through-opening in said second wall element;
- at least one tubular element coaxially connecting said inlet and outlet through-openings; and
- a reference resonator in which said tubular element is, in use, free from textile fibre material;
- wherein the housing comprises a hollow profile with profile walls of which first and second opposite profile walls of the hollow profile form said first and second wall elements in which said connected through-openings are located.

18. A microwave resonator for or on a textile machine for attachment to a measuring device for measuring the mass and/or moisture content of textile fibre material comprising:
- a resonator chamber through which textile fibre material is conveyable continuously, having a housing with wall elements including spaced, opposed first and second wall elements;
- an inlet through-opening in said first wall element and an outlet through-opening in said second wall element; and
- at least one tubular element coaxially connecting said inlet and outlet through-openings;
- wherein the housing comprises a hollow profile with profile walls of which first and second opposite profile walls of the hollow profile form said first and second wall elements in which said connected through-openings are located;
- further wherein at least one end of the tubular element is provided with an outwardly flared member, forming respectively, an inlet funnel element that is flared outwardly to form an inlet funnel portion that converges in the direction of travel of the fibre material and/or an outlet funnel element that is flared outwardly to form an outlet funnel portion that diverges in the direction of travel of the fibre material.

19. A microwave resonator according to claim 18, in which the inlet funnel element and/or outlet funnel element are arranged outside the resonator chamber or in the region of the outer walls of the hollow profile.

20. A microwave resonator according to claim 18, in which the tubular element and the inlet funnel element and/or outlet funnel element comprise the same material and are formed in one piece.

21. A microwave resonator according to claim 18, in which the tubular element and the inlet funnel element and/or outlet funnel element are formed in at least two pieces.

22. A microwave resonator according to claim 18, in which there can be used alternative tubular elements with different internal diameters.

23. A microwave resonator for or on a textile machine for attachment to a measuring device for measuring the mass and/or moisture content of textile fibre material comprising:
- a resonator chamber through which textile fibre material is conveyable continuously, having a housing with wall elements including spaced, opposed first and second wall elements;
- an inlet through-opening in said first wall element and an outlet through-opening in said second wall element;
- at least one tubular element coaxially connecting said inlet and outlet through-openings; and
- a reference resonator, the reference resonator and the measuring resonator being accommodated in a common, closed housing and being continuously flushed with air for temperature equalization;
- wherein the housing comprises a hollow profile with profile walls of which first and second opposite profile walls of the hollow profile form said first and second wall elements in which said connected through-openings are located.

24. A microwave resonator according to claim 23, in which the measuring resonator on the one hand and the reference resonator on the other hand are two independently separate components.

25. A microwave resonator according to claim 23, in which the measuring resonator and the reference resonator are a one-piece component, in which a partition wall is arranged.

26. A microwave resonator for or on a textile machine for attachment to a measuring device for measuring the mass and/or moisture content of textile fibre material comprising:
- a resonator chamber through which textile fibre material is conveyable continuously, having a housing with wall elements including spaced, opposed first and second wall elements;
- an inlet through-opening in said first wall element and an outlet through-opening in said second wall element; and
- at least one tubular element coaxially connecting said inlet and outlet through-openings;
- an electronic control and regulating device connected to the microwave resonator; and
- an actuating device for a variable speed device motor connected to the electronic control and regulating device, the actuating device for the variable speed device motor adapted to alter the thickness of a fibre silver;
- wherein the housing comprises a hollow profile with profile walls of which first and second opposite profile walls of the hollow profile form said first and second wall elements in which said connected through-openings are located.

* * * * *